United States Patent
Takiwaki et al.

(10) Patent No.: US 11,927,510 B2
(45) Date of Patent: Mar. 12, 2024

(54) STANDARD CALIBRATION SOLUTION

(71) Applicant: JEOL Ltd., Tokyo (JP)

(72) Inventors: Masaki Takiwaki, Tokyo (JP); Seketsu Fukuzawa, Tokyo (JP); Yoshikuni Kikutani, Tokyo (JP); Kiyotaka Fujino, Tokyo (JP); Kentaro Abe, Tokyo (JP); Yoshiyuki Ito, Tokyo (JP)

(73) Assignee: JEOL Ltd., Tokyo (JP)

( * ) Notice: Subject to any disclaimer, the term of this patent is extended or adjusted under 35 U.S.C. 154(b) by 148 days.

(21) Appl. No.: 16/953,502

(22) Filed: Nov. 20, 2020

(65) Prior Publication Data

US 2021/0156770 A1    May 27, 2021

(30) Foreign Application Priority Data

Nov. 21, 2019    (JP) .................. 2019-210188

(51) Int. Cl.
*G01N 1/28* (2006.01)
*G01N 33/74* (2006.01)
*G01N 33/82* (2006.01)

(52) U.S. Cl.
CPC ............. *G01N 1/28* (2013.01); *G01N 33/743* (2013.01); *G01N 33/82* (2013.01); *G01N 2001/2893* (2013.01); *Y10T 436/104165* (2015.01)

(58) Field of Classification Search
CPC .. Y10T 436/104165; G01N 2001/2893; G01N 33/743; G01N 33/82
See application file for complete search history.

(56) References Cited

U.S. PATENT DOCUMENTS

| | | |
|---|---|---|
| 2002/0064883 A1 | 5/2002 | Jia et al. |
| 2008/0000771 A1 | 1/2008 | Kakiuchi et al. |
| 2009/0137056 A1 | 5/2009 | Holmquist et al. |
| 2011/0226945 A1 | 9/2011 | Holmquist et al. |
| 2012/0190121 A1 | 7/2012 | Holmquist et al. |
| 2013/0143329 A1 | 6/2013 | Holmquist et al. |
| 2014/0234989 A1 | 8/2014 | Holmquist et al. |
| 2020/0158688 A1 | 5/2020 | Holmquist et al. |

FOREIGN PATENT DOCUMENTS

| | | | |
|---|---|---|---|
| CN | 104215716 A | | 12/2014 |
| CN | 106908554 A | * | 6/2017 |
| CN | 109470791 A | | 3/2019 |
| JP | 2019179036 A | | 10/2019 |

OTHER PUBLICATIONS

Sýs, M. et al. "Adsorptive stripping voltammetry in lipophilic vitamins determination," Potravinarstvo, vol. 10, 2016, No. 1, p. 260-264 (Year: 2016).*
Mata-Granados, J.M. et al. "Fully automatic method for the determination of fat soluble vitamins and vitamin D metabolites in serum," Clinica Chimica Acta 403 (2009) 126-130 (Year: 2009).*
Henderson Jr., J.W. et al. "UHPLC Method Development Options for a Vitamin D2 and D3 Separation," Application Note: Food, Agilent Technologies 2009 (Year: 2009).*
Extended European Search Report issued in EP20208682.3 dated Apr. 23, 2021.
Hauser et al., Development of a liquid chromatography-tandem mass spectrometry method for the determination of 23 endogenous steroids in small quantities of primate urine, Journal of Chromatography B, 2008, vol. 862, pp. 100-112.
Wei et al., In-Tip Solid Phase Microextraction for High Throughput Drug Analysis, 2011, pp. 96-134; retrieved at: https://uwspace.uwaterloo.ca/bitstream/handle/10012/6338/Xie_Wei.pdf?sequence=1&isAllowed=y.
Latreille and Banquy, A simple method for the subnanomolar quantitation of seven opthalmic drugs in the rabbit eye, Analytical and Bioanalytical Chemistry, 2015, vol. 407, pp. 3567-3578.
Zuehlke et al., Determination of estrogenic steroids in surface water and wastewater by liquid chromatography-electrospray tandem mass spectrometry, Journal of Separation Science, vol. 28, No. 1, 2005, pp. 52-58.
Office Action issued in JP 2019-210188 dated Nov. 2, 2021.
Communication issued in EP20208682.3 dated Oct. 7, 2022.
Marta et al., Simultaneous determination of thirteen different steroid hormones using micro UHPLC-MS/MS with on-line SPE system, Journal of Pharmaceutical and Biomedical Analysis, 2018, vol. 150, pp. 258-267.

* cited by examiner

*Primary Examiner* — Jennifer Wecker
*Assistant Examiner* — Michelle Adams
(74) *Attorney, Agent, or Firm* — The Webb Law Firm

(57) ABSTRACT

A standard calibration solution includes water, a non-alcoholic solvent that is mixed with water, and a steroid hormone, and a content of the non-alcoholic solvent is 10% by volume or more and 50% by volume or less. The standard calibration solution is used for quantitative measurement using a mass spectrometry device.

6 Claims, 6 Drawing Sheets

STANDARD CALIBRATION SOLUTION

CROSS-REFERENCE TO RELATED APPLICATION

This application claims priority to Japanese Patent Application No. 2019-210188 filed Nov. 21, 2019, the disclosure of which is hereby incorporated by reference in its entirety.

BACKGROUND OF THE INVENTION

Field of the Invention

The present invention relates to a standard calibration solution suitable for quantitative measurement using a mass spectrometry device.

Description of Related Art

In clinical examinations at hospitals, or the like, an analysis method using a mass spectrometer (which will be hereinafter also referred to as "MS") is known. Particularly, analysis of a substance derived from an organism, such as a hormone, by a liquid chromatography/mass spectrometer (which will be hereinafter also referred to as "LC/MS") that separates a compound by high performance liquid chromatography (HPLC), and ionizes the separated substance by a MS in order to implement analysis exhibits higher sensitivity and higher specificity than those of conventionally used immunoassay, or the like, and moreover is capable of simultaneous analysis of multiple items. Hence, this analysis has become a mainstream rapidly. In quantitative analysis by LC/MS/MS using, in particular, a tandem mass spectrometer (which will be hereinafter also referred to as "MS/MS") as a MS from among LC/MSs, use of a selected or multiple reaction monitoring (which will be hereinafter also referred to as "SRM" or "MRM") mode, which exhibits higher sensitivity than that of a LC/MS, enables selective quantitative analysis of a plurality of substances.

Quantitative analysis by a MS is generally carried out based on a calibration curve using a standard calibration solution, which is referred to as a calibrator. For example, in JP-A-2019-179036, by using a calibrator including an isotope of a dihydroxy vitamin D metabolite as an internal reference material, a calibration standard curve based on one or more peaks of the internal reference material is formed. This patent documents further discloses that the peak obtained from measurement of the dihydroxy vitamin D metabolite is converted to an absolute amount based on such a calibration standard curve, thereby performing quantitative analysis.

However, the calibrator including the internal reference material as disclosed in JP-A-2019-179036 is supplied as a liquid using serum as a solvent. In a case where serum is used as the solvent of a calibrator, the serum is preferably sufficiently purified for use. However, it is not always easy to completely remove an endogenous substance derived from an organism. When a substance derived from an organism that equates to an analyte is present, satisfactory calibration may not be able to be performed.

With serum and plasma that derive from animals being supplied, it is difficult to eliminate individual differences among animals and variations in quality among production lots, and moreover protein contained therein may be deteriorated. Variation in quality may adversely affect the calibration for quantitative analysis.

SUMMARY OF THE INVENTION

The invention is able to provide a standard calibration solution having stable quality capable of performing calibration with high precision in quantitative measurement using a mass spectrometry device.

According to one aspect of the invention, there is provided a standard calibration solution including:
water;
a non-alcoholic solvent that is mixed with the water; and
a steroid hormone,
a content of the non-alcoholic solvent being 10% by volume or more and 50% by volume or less, and
the standard calibration solution being used for quantitative measurement using a mass spectrometry device.

DESCRIPTION OF THE INVENTION

Figure 1:
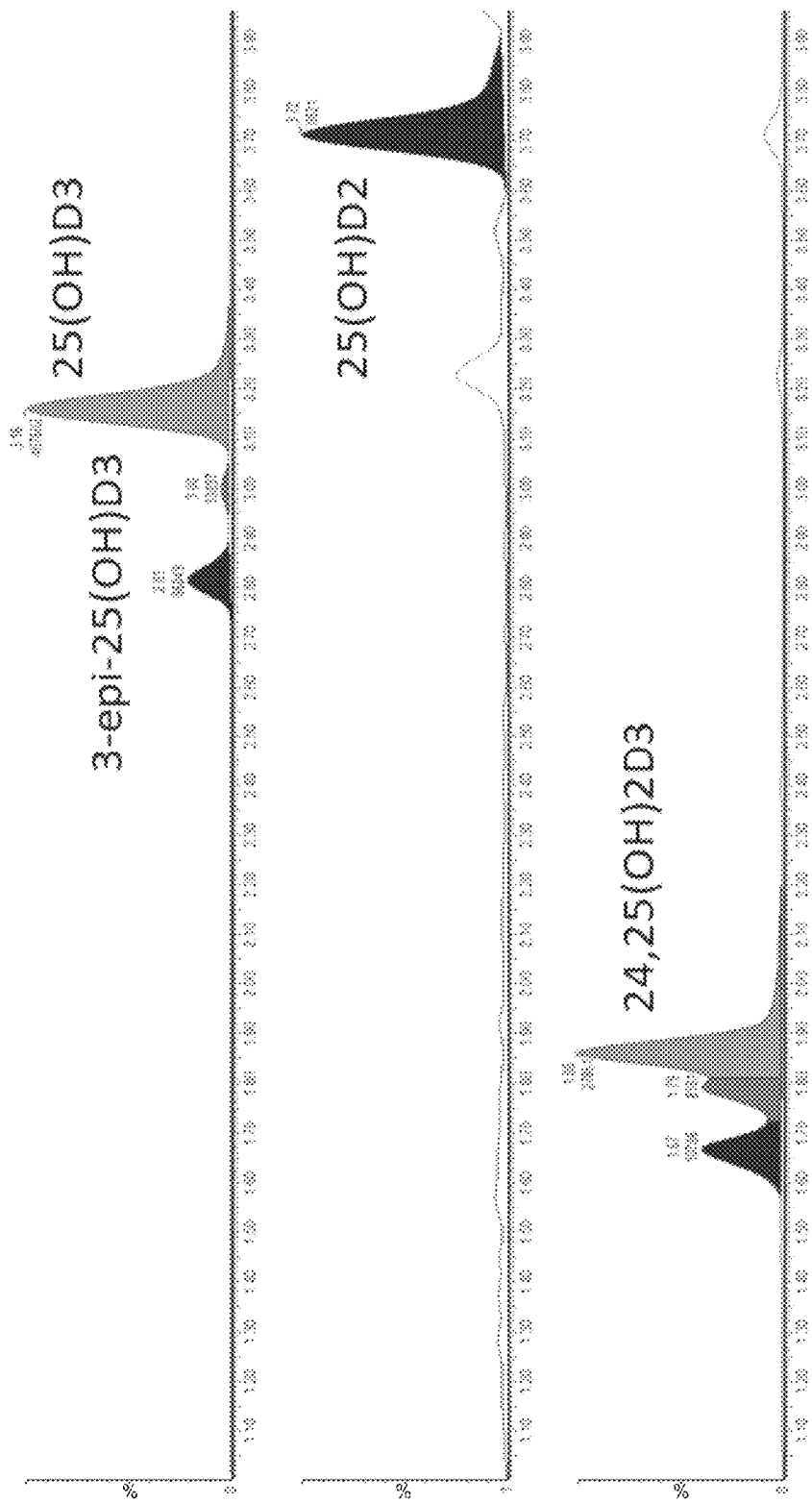
FIG. 1 illustrates an MRM chromatogram of a vitamin D metabolite in accordance with Experimental Example.
Figure 2:
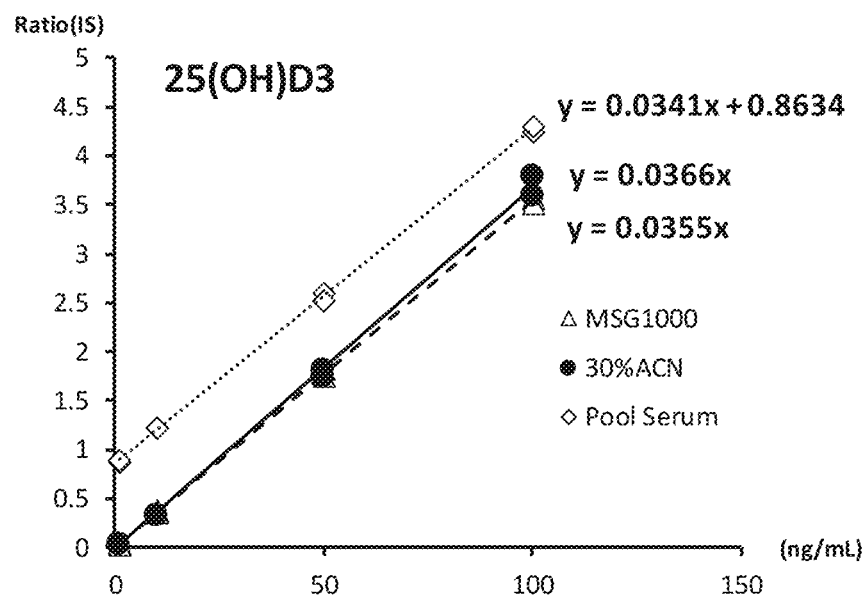
FIG. 2 is a graph of a calibration curve of 25(OH)$D_3$ in accordance with Experimental Example.
Figure 3:
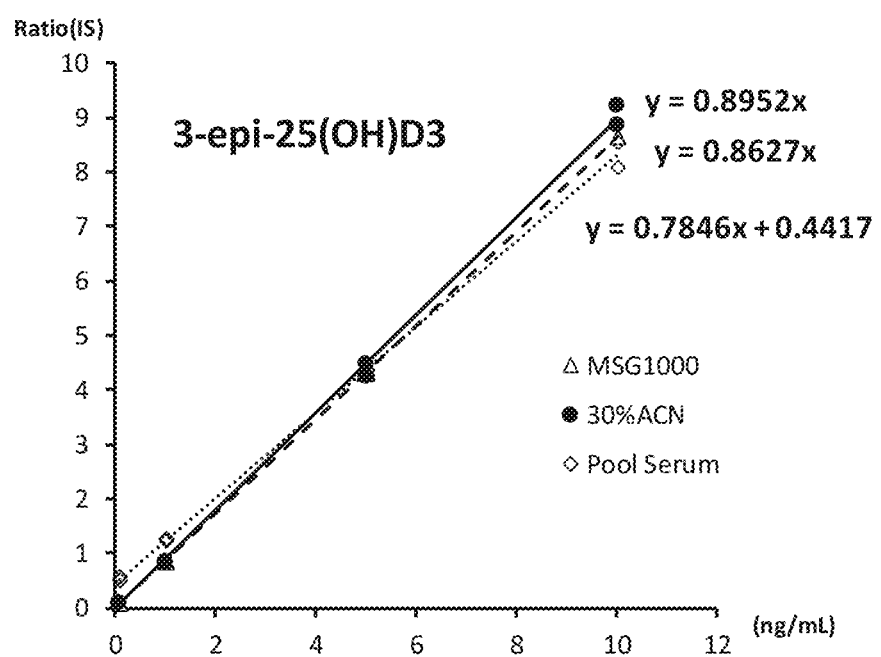
FIG. 3 is a graph of a calibration curve of 3-epi-25(OH)$D_3$ in accordance with Experimental Example.
Figure 4:
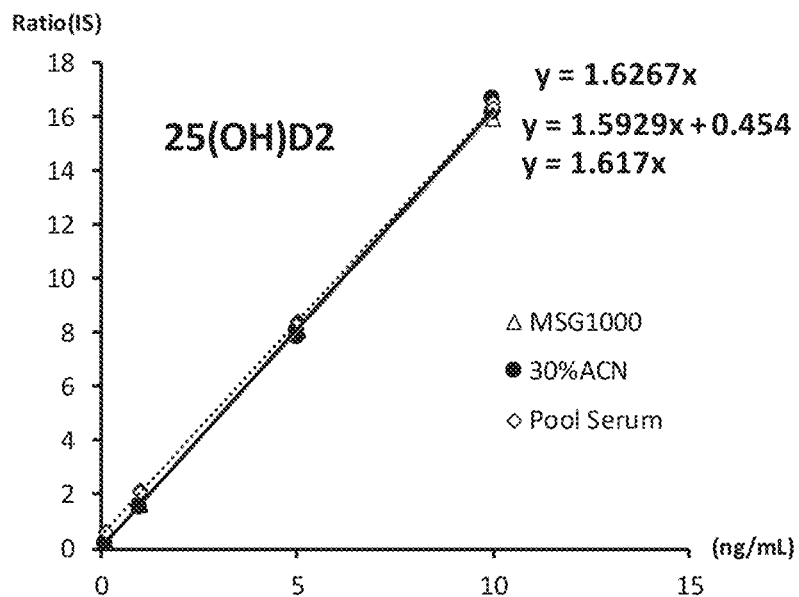
FIG. 4 is a graph of a calibration curve of 25(OH)$D_2$ in accordance with Experimental Example.
Figure 5:
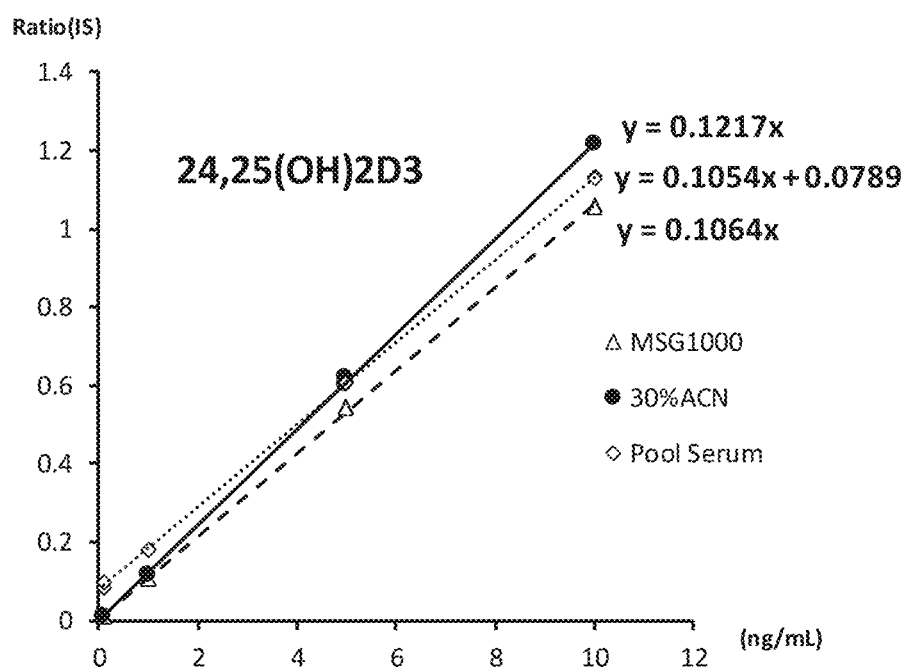
FIG. 5 is a graph of a calibration curve of 24,25(OH)2D3 in accordance with Experimental Example.
Figure 6:
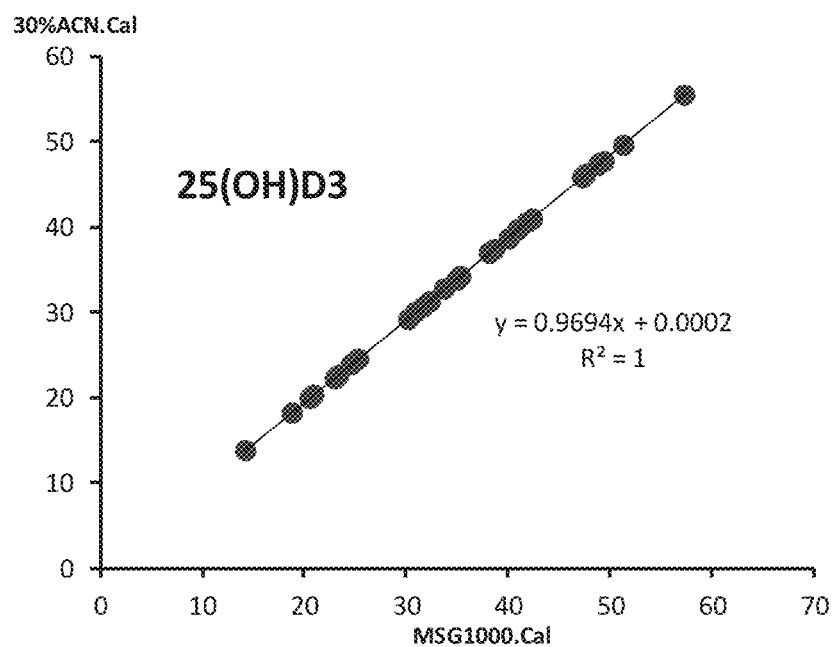
FIG. 6 is a graph illustrating the correlation of the quantitative results in a clinical specimen (of 25(OH)$D_3$) between when an acetonitrile aqueous solution is used as a medium and when serum is used as a medium.
Figure 7:
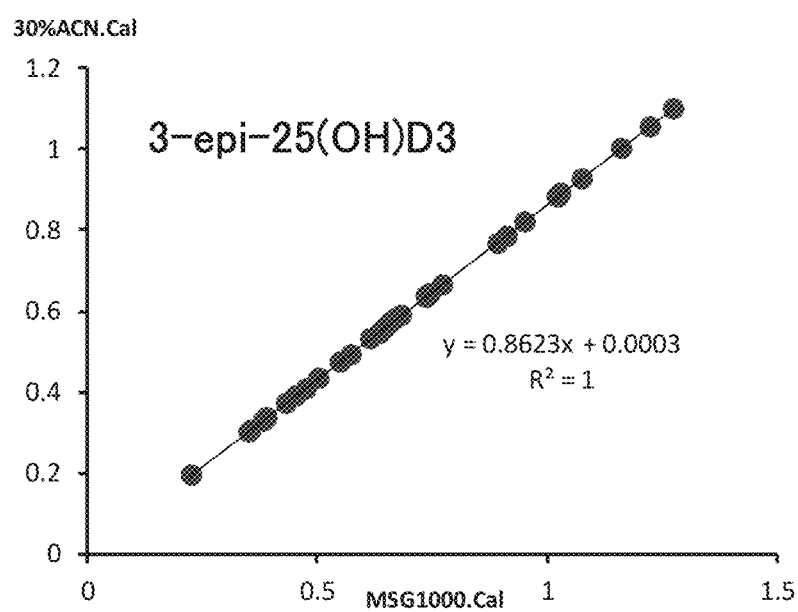
FIG. 7 is a graph illustrating the correlation of the quantitative results in a clinical specimen (of 3-epi-25(OH)$D_3$) between when an acetonitrile aqueous solution is used as a medium and when serum is used as a medium.
Figure 8:
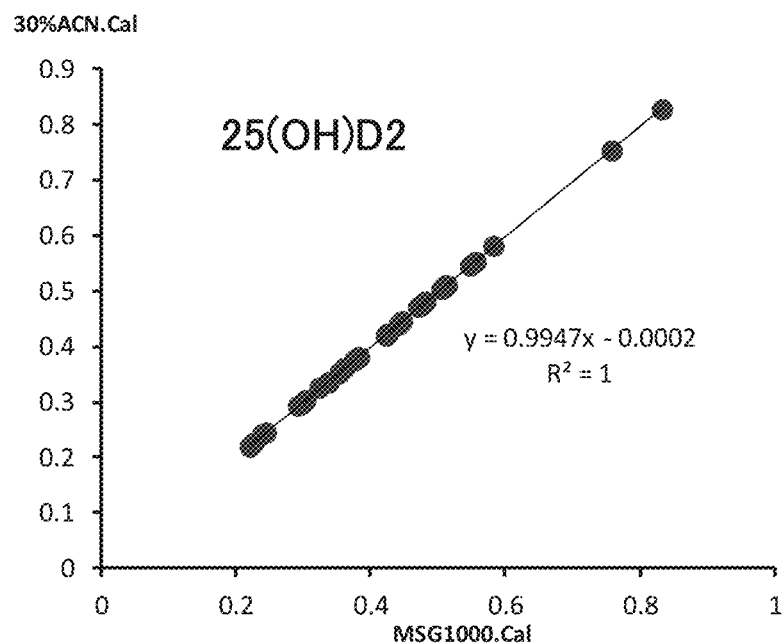
FIG. 8 is a graph illustrating the correlation of the quantitative results in a clinical specimen (of 25(OH)$D_2$) between when an acetonitrile aqueous solution is used as a medium and when serum is used as a medium.
Figure 9:
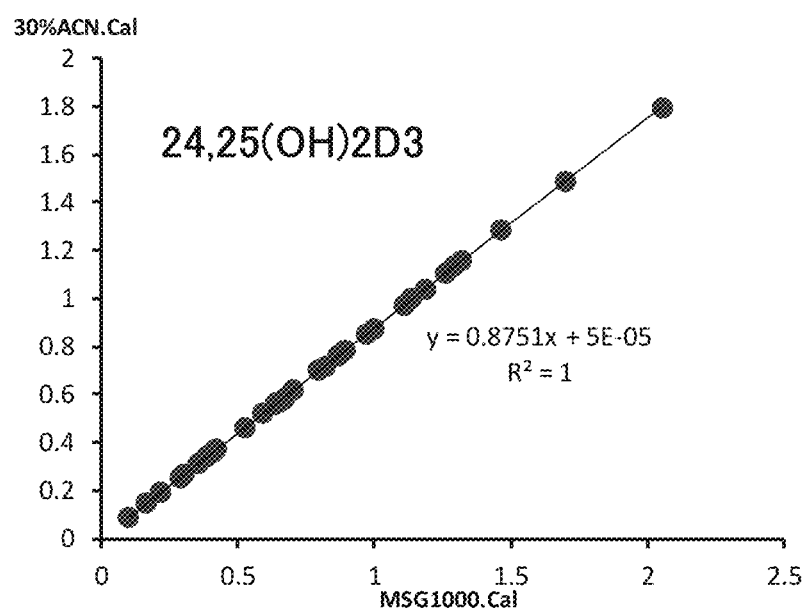
FIG. 9 is a graph illustrating the correlation of the quantitative results in a clinical specimen (of 24,25(OH)$_2D_3$) between when an acetonitrile aqueous solution is used as a medium and when serum is used as a medium.

The invention was completed in order to solve at least a part of the problem, and can be implemented as the following applied example.

According to one embodiment of the invention, there is provided a standard calibration solution including:
water;
a non-alcoholic solvent that is mixed with the water; and
a steroid hormone,
a content of the non-alcoholic solvent being 10% by volume or more and 50% by volume or less, and
the standard calibration solution being used for quantitative measurement using a mass spectrometry device.

The standard calibration solution is favorable in stability of the quality, and can perform high-precision calibration in quantitative measurement using a mass spectrometry device.

Some embodiments of the invention will be described below. The embodiments below describe examples of the invention. The invention is not limited to the following embodiments at all, and also includes various modifications to be executed without changing the scope of the invention. In addition, all of the elements described below are not necessarily essential requirements of the invention.

1. STANDARD CALIBRATION SOLUTION

The standard calibration solution in accordance with one embodiment of the invention includes water, a non-alcoholic solvent to be mixed with water, and a steroid hormone. Then, the content of the non-alcoholic solvent is 10% by volume or more and 50% by volume or less for every 100% by volume of the total amount of the standard calibration solution. The standard calibration solution of the present embodiment is used for quantitative measurement using a mass spectrometry device, and can be used as a "calibrator" for mass spectroscopy. Below, the components and uses of the standard calibration solution of the present embodiment will be successively described.

1.1. Water

The standard calibration solution in accordance with the present embodiment includes water. As water, for example, ion exchanged water, ultrafiltration water, reverse osmosis water, or Milli-Q water can be used. The water preferably has the minimum amount of impurities, and preferably satisfies the standards of, for example, water for analysis experiment, and biomedical water.

The content of water in the standard calibration solution is preferably 50% by volume or more and 90% by volume or less, more preferably 60% by volume or more and 80% by volume or less, and further preferably 65% by volume or more and 75% by volume or less based on the total amount (100% by volume) of the standard calibration solution. When the content of water is about 50% by volume or more and 90% by volume or less, various steroid hormones can be dissolved therein.

1.2. Non-Alcoholic Solvent

The standard calibration solution in accordance with the present embodiment includes a non-alcoholic solvent. The non-alcoholic solvent is a compound not having an alcoholic hydroxy group. The non-alcoholic solvent is mixed with the water at an arbitrary ratio. Namely, the non-alcoholic solvent and water are fully dissolved in each other in an arbitrary concentration, and can form a uniform solution.

The content of the non-alcoholic solvent in the standard calibration solution is 10% by volume or more and 50% by volume or less. Further, the content of the non-alcoholic solvent in the standard calibration solution can be adjusted in consideration of the properties (such as water solubility and fat solubility), and the like of the steroid hormone included in the standard calibration solution. For example, when the fat solubility of the steroid hormone is relatively strong, the content of the non-alcoholic solvent is more preferably 20% by volume or more and 50% by volume or less, and further preferably 20% by volume or more and 40% by volume or less. Whereas, conversely, when the water solubility of the steroid hormone is relatively strong, the content of the non-alcoholic solvent is more preferably 10% by volume or more and 40% by volume or less, and still more preferably 10% by volume or more and 35% by volume or less.

Thus, the content of the non-alcoholic solvent in the standard calibration solution can be adjusted by the properties of the included steroid hormone, or the like. A small content thereof tends to be suitable for a steroid hormone with strong water solubility, and a large content thereof tends to be suitable for a steroid hormone with strong fat solubility.

More specific examples of the non-alcoholic solvent may include a compound having 5 or less carbon atoms and having at least one group selected from a cyano group, a carbonyl group, an ether group, and a sulfinyl group. Further, such a compound may include one or a plurality of the same kind of or different kinds of groups of a cyano group, a carbonyl group, an ether group, and a sulfinyl group. Specific examples of such a compound may include acetonitrile ($CH_3$—CN), acetone ($(CH_3)_2C=O$), dimethylformamide ($(CH_3)_2N$—CHO), dimethylacetamide ($(CH_3)_2N$—$COCH_3$), tetrahydrofuran, dioxane, and dimethyl sulfoxide ($(CH_3)_2S=O$). Further, the number of carbons of the compound is more preferably 1 or more and 4 or less, and further preferably 1 or more and 2 or less.

As demonstrated in Experimental Example described later, the non-alcoholic solvent is further preferably a compound having 2 or less carbon atoms, and having one cyano group. The cyano group is a group with high degree of polarization, and can efficiently impart the polarity to the compound by being coordinated to a carbon atom. Also, from such a reason, the non-alcoholic solvent is especially preferably acetonitrile.

1.3. Steroid Hormone

The standard calibration solution of the present embodiment includes a steroid hormone. As steroid hormones, mention may be made of adrenal cortical hormone or sex hormone such as aldosterone (mineral corticoid), testosterone, cortisol (hydrocortisone), cortisone, progesterone, hydroxy progesterone, prednisone, androstenedione, glucocorticoid, androgen (male sex hormone), estrogen (female sex hormone), or corpus luteum hormone, and vitamin D, and a metabolite, a derivative, and an isotope-labelled product thereof.

Herein, vitamin D is fat-soluble vitamin essential for adjustment of calcium metabolism, and has an action of increasing the calcium ($Ca^{2+}$) concentration in blood as the active form of vitamin D ($1\alpha,25$-dihydroxyvitamin D). In addition to this action, an in vivo metabolite such as 1,25-dihydroxyvitamin D or 25-hydroxyvitamin D plays an important role in control of expression of protein involved in differentiation/growth of cell, production/secretion of hormone, an immune reaction, or the like. For this reason, from the viewpoint of the mechanism of action and function, in the present specification, vitamin D, the derivative of vitamin D, the metabolite of vitamin D, and the isotope-labelled product of vitamin D are regarded as steroid hormones although they are sterol in terms of chemical structure.

The standard calibration solution of the present embodiment may include one or a plurality of steroid hormones.

Further, the steroid hormone included in the standard calibration solution of the present embodiment is more preferably fat soluble, and is further preferably at least one selected from vitamin D and the metabolite of vitamin D, and testosterone and the metabolite of testosterone of the fat soluble steroid hormones.

The steroid hormone included in the standard calibration solution is set at a specific concentration for use as a standard calibration solution. Such a specific concentration is set according to the necessity in forming the calibration curve of mass spectrometry, and the range of the configurable concentration has no particular restriction.

1.4. Use of Standard Calibration Solution

The standard calibration solution of the present embodiment is used for the quantitative measurement using a mass spectrometry device.

Mass spectrometry is a method for separating, detecting, and measuring ions based on the mass electric charge ratio or "Da/e". Generally, the analyte compound is ionized, and is loaded into a mass spectrometry device. The method of ionization has no particular restriction. In the mass spectrometry device, ions follow the path in the space according to the mass and the electric charges by the combination of the magnetic field and the electric field. Then, by observing the mass, the electric charge, the behavior, and the like of the ions in the mass spectrometry device, it is possible to perform detection and quantification of the analyte compound.

As the specimens to be subjected to mass spectrometry, mention may be made of the components obtained from biological sources such as animals, cell culture, and organ culture. More specifically, mention may be made of the samples obtained from human, for example, blood, plasma, deproteinized plasma, serum, sputum, muscle, urine, saliva, lachrymal fluid, cerebrospinal fluid, swab from the body portion, a microorganism suspension, or a tissue sample.

The mass spectrometry may be performed by combining various separation and purification means. For example, mass spectrometry can be combined with the operations of filtration, extraction, precipitation, centrifugation, dilution, and the like. Particularly, before analysis by mass spectrometry, purification or clarification may be performed, and the analyte compound may be more enriched than other compounds to be subjected to mass spectrometry. The means for performing this may include, but not limited to, liquid chromatography, HPLC, UHPLC, precipitation, dialysis, affinity/capture, electrophoresis, or proper methods known in the technical field. Examples of the device undergoing such a combination may include "LC/MS" of a combination with HPLC, and "LC/MS/MS" obtained by forming a mass spectrometry part in a tandem model.

When quantitative analysis by a mass spectrometry device is performed, careful calibration is necessary for isolating and identifying the analyte compound. The standard calibration solution of the present embodiment can be preferably used for such calibration.

The standard calibration solution of the present embodiment can be used for forming the calibration curve of a mass spectrometer, and can be used, for example, for obtaining the calibration curve of the dependency of the signal intensity on the concentration of a steroid hormone before the measurement of the steroid hormone.

Conventionally, for calibration in LC/MS/MS of a hormone, a solution of a calibration substance dissolved in the same medium as the measurement specimen (biological preparation) such as serum or plasma, or a solution of calibration substance dissolved in an artificial medium such as hydrous ethanol or hydrous methanol has been used.

The former has an advantage that the measurement environment is close to an organism. However, in the case of an originally endogenous analyte such as a hormone, after once removing it, the analyte is added to be valued. In this case, undesirably, it was difficult to remove the endogenous substance with reliability, and it was difficult to guarantee the precision of the calibrator. In the latter case, the endogenous substance like hormone is not required to be considered. Instead, the matrix effect has become a problem in terms of the similarity to the medium of the specimen such as serum.

The standard calibration solution of the present embodiment includes the non-alcoholic solvent, and a steroid hormone. A content of the non-alcoholic solvent of 10% by volume or more and 50% by volume or less enables the formation of the calibration curve serving as the basis of quantification by the clinical examination field, particularly the mass spectrometry of in vivo hormone/drug with ease and with good reproducibility. Further, as the solvent, a non-alcoholic solvent is used. For this reason, the composition of the standard calibration solution less changes with time, and the quality of the raw material is stable. Accordingly, the restriction on the freshness, the storage period, or the like is relaxed. Further, for this reason, the standard calibration solution of the present embodiment can be preferably used for calibration of each device irrespective of the difference in manufacturer of the mass spectrometry device, the variations among individual devices and components, and the like. Further, the standard calibration solution of the present embodiment can readily form a calibration curve with good precision as with the case using a favorably controlled solution of a calibration substance (biological preparation) using serum, plasma, or the like as the medium conventionally used.

On the other hand, the standard calibration solution of the present embodiment is also further preferably applicable to an analysis system including a mass spectrometry device such as LC/MS/MS. The solution of calibration substance dissolved in artificial medium such as hydrous ethanol or hydrous methanol conventionally used has a strong elution force with respect to a reversed-phase silica column generally for use in LC, and may not be adsorbed on the column, or may cause deterioration of peak separation due to peak broadening. For this reason, it has been necessary to once distill away alcohol (solvent displacement), and redissolve the extract in the solvent of the initial conditions of LC.

In contrast, the standard calibration solution of the present embodiment can be loaded into LC without performing the operation such as distillation, and can form an excellent calibration curve. Incidentally, the medium of the mobile phase of LC has a difference object from that of the standard calibration solution of the present embodiment. Even when a liquid with the same composition as that of the standard calibration solution of the present embodiment is generated in the LC column, the liquid cannot function as a standard calibration solution. Further, the standard calibration solution of the present embodiment is different from the liquid present in the mobile phase in the LC column in terms of being able to be accommodated and stored in an appropriate container.

1.5. Advantageous Effects and the Like

The standard calibration solution of the present embodiment can make the difference among the production lots smaller, can keep stable quality, and can perform calibration of a mass spectrometry device with ease and with good reproducibility as compared with the calibration solution using the medium derived from an organism such as serum. Further, the standard calibration solution of the present embodiment includes a non-alcoholic solvent, and hence has a gentler elution force with respect to the reversed-phase silica column than that of an alcoholic solvent such as ethanol or methanol, and can be loaded as it is into a LC/MS or a LC/MS/MS without performing solvent displacement.

2. EXPERIMENTAL EXAMPLES

Below, the invention will be specifically described by way of Experimental Examples. However, the invention is not limited to the Experimental Examples. Below, "%" regarding the solvent is on a volume basis unless otherwise specified. Incidentally, the evaluation was performed under environment of a temperature of 25° C., and a relative humidity of 40% unless otherwise specified.

2.1. Verification of Calibration Curve

Whether the difference in solvent (matrix) affected the calibration curve or not for preparing a standard calibration solution was verified by the following experiments.

2.1.1. Used Solvent

The following solvents a) to c) were prepared.

a) MSG1000 (available from Golden West Diagnostics, LLC) vitamin D free serum b) 30% acetonitrile aqueous solution c) Pooled serum (available from Chiba University Hospital healthy volunteer)

2.1.2. Preparation of Standard Calibration Solution and Calibration Curve Formation Procedure (1) The samples of the steroid hormone (metabolite of vitamin D) described in Table 1 were dissolved in the respective solvents, thereby preparing respective calibrators so as to achieve the respective calibrator concentrations shown in Table 1.

TABLE 1

Calibrator concentration (each sample added)

|  | $25(OH)D_3$ | 3-epi-$25(OH)D_3$ | $25(OH)D_2$ | 24,25-$(OH)_2D_3$ |
|---|---|---|---|---|
| Concentration (ng/mL) | 1 | 0.1 | 0.1 | 0.1 |
|  | 10 | 1 | 1 | 1 |
|  | 50 | 5 | 5 | 5 |
|  | 100 | 10 | 10 | 10 |

(2) An internal reference material was added to each calibrator adjusted in concentration, and a pretreatment was performed by Supported Liquid Extraction (SLE). Incidentally, the internal reference materials are specifically as follows.

$25(OH)D_3$-$^{13}C_5$ 3-epi-$25(OH)D_3$-$^{13}C_5$ $25(OH)D_2$-$^{13}C_3$ $24,25(OH)_2D_3$-$d_6$ (3) The extract obtained in the pretreatment was evaporated to dryness under nitrogen, followed by addition of 4-(4'-dimethylamino phenyl)-1,2,4-triazoline-3,5-dione (DAPTAD) thereto, and the resulting mixture was allowed to react at room temperature for 60 minutes.

(4) Ethanol was added thereto, and after terminating the reaction, the solution was evaporated to dryness under nitrogen.

(5) The resulting residue was redissolved in a 30% acetonitrile solution, to be used as a specimen for LC/MS analysis.

(6) The resulting specimen was loaded to a LC/MS/MS (Xevo TQ-XS, Waters), and quantitative analysis was performed using the multiple reaction monitoring (MRM) parameters described in Table 2. FIG. 1 illustrates the MRM chromatogram of the vitamin D metabolite.

(7) The calibration curve was formed using the peak area ratio of the internal reference material in the calibrator and an analyte compound.

TABLE 2

MRM parameters of vitamin D metabolite

| Test substance | MRM(m/z) |
|---|---|
| $25(OH)D_3$ | 619.4 < 341.2 |
| 3-epi-$25(OH)D_3$ | 631.4 < 341.2 |
| $25(OH)D_2$ | 635.2 < 341.2 |
| $24,25$-$(OH)_2D_3$ | 619.4 < 341.2 |

2.2. Calibration Curve and Evaluation of Precision

The calibration curves obtained above are illustrated in FIGS. 2 to 5. Referring to FIGS. 2 to 5, with four kinds of vitamin D metabolites, the effect on the calibration curve (change in gradient) due to the difference in solvent was not observed.

2.3. Recovery Test by Pooled Serum

A sample was added to a pooled serum, thereby conducting a recovery test. With two ways using MSG1000 and a 30% acetonitrile aqueous solution as the solvent of the calibrator, calibration curves were formed. The effects on the quantitative value by the difference in calibrator solvent were verified. Tables 3 to 6 show the results.

TABLE 3

$25(OH)D_3$

| Spiked conc. | Expected conc. (pg/mL) | Measured conc. (pg/mL) | Recovery conc. (pg/mL) | Recovery (%) |
|---|---|---|---|---|
| MSG1000•Cal | | | | |
| Endogenous baseline | — | 23.9 | — | — |
| 10 ng/mL | 33.9 | 34.6 | 10.7 | 107 |
| 50 ng/mL | 73.9 | 72.1 | 48.2 | 96.4 |
| 100 ng/mL | 123.9 | 120.6 | 96.7 | 96.7 |
| 30% ACN•Cal | | | | |
| Endogenous baseline | — | 23.1 | — | — |
| 10 ng/mL | 33.9 | 33.5 | 10.4 | 104 |
| 50 ng/mL | 73.9 | 69.8 | 46.7 | 93.4 |
| 100 ng/mL | 123.9 | 116.9 | 93.8 | 93.8 |

TABLE 4

3-epi-$25(OH)D_3$

| Spiked conc. | Expected conc. (pg/mL) | Measured conc. (pg/mL) | Recovery conc. (pg/mL) | Recovery (%) |
|---|---|---|---|---|
| MSG1000•Cal | | | | |
| Endogenous baseline | — | 0.523 | — | — |
| 1 ng/mL | 1.52 | 1.44 | 0.92 | 92 |
| 5 ng/mL | 5.52 | 4.98 | 4.5 | 90 |
| 10 ng/mL | 10.52 | 9.64 | 9.1 | 91 |
| 30% ACN•Cal | | | | |
| Endogenous baseline | — | 0.5 | — | — |
| 1 ng/mL | 1.5 | 1.39 | 0.89 | 89 |
| 5 ng/mL | 5.5 | 4.8 | 4.3 | 86 |
| 10 ng/mL | 10.5 | 9.3 | 8.8 | 88 |

TABLE 5

25(OH)D$_2$

| Spiked conc. | Expected conc. (pg/mL) | Measured conc. (pg/mL) | Recovery conc. (pg/mL) | Recovery (%) |
|---|---|---|---|---|
| MSG1000•Cal | | | | |
| Endogenous baseline | — | 0.257 | — | — |
| 1 ng/mL | 1.26 | 1.31 | 1.05 | 105 |
| 5 ng/mL | 5.26 | 5.17 | 4.91 | 98.2 |
| 10 ng/mL | 10.26 | 10.14 | 9.89 | 98.9 |
| 30% ACN•Cal | | | | |
| Endogenous baseline | — | 0.255 | — | — |
| 1 ng/mL | 1.255 | 1.3 | 1.05 | 104.6 |
| 5 ng/mL | 5.255 | 5.14 | 4.88 | 97.6 |
| 10 ng/mL | 10.255 | 10.08 | 9.82 | 98.2 |

TABLE 6

24,25(OH)$_2$D$_3$

| Spiked conc. | Expected conc. (pg/mL) | Measured conc. (pg/mL) | Recovery conc. (pg/mL) | Recovery (%) |
|---|---|---|---|---|
| MSG1000•Cal | | | | |
| Endogenous baseline | — | 0.759 | — | — |
| 1 ng/mL | 1.76 | 1.7 | 0.94 | 94 |
| 5 ng/mL | 5.76 | 5.7 | 4.95 | 99 |
| 10 ng/mL | 10.76 | 10.63 | 9.88 | 98.8 |
| 30% ACN•Cal | | | | |
| Endogenous baseline | — | 0.652 | — | — |
| 1 ng/mL | 1.652 | 1.48 | 0.837 | 83.7 |
| 5 ng/mL | 5.652 | 4.99 | 4.34 | 86.8 |
| 10 ng/mL | 10.652 | 9.31 | 8.65 | 86.5 |

Referring to Tables 3 to 6, it has been indicated as follows: use of either calibration curve formed by two different calibrators using MSG1000 and a 30% acetonitrile aqueous solution as the solvent of the calibrator does not cause a big difference in quantitative value, and can provide a favorable recovery rate.

2.4. Quantitative Analysis of Clinical Specimen

The vitamin D metabolites in the serums of the clinical specimens (32 examples) were quantitatively analyzed by two different calibration curves using different calibrator solvents (MSG1000 and a 30% acetonitrile aqueous solution). FIGS. 6 to 9 are each a graph illustrating the correlation between the quantitative analysis values of the clinical specimens obtained by two different calibration curves. As illustrated in FIGS. 6 to 9, the correlation between the quantitative values obtained from the two different calibration curves was checked, indicating the favorable correlation and the agreement between the quantitative values.

2.5. Evaluation of Testosterone

Figure 10:
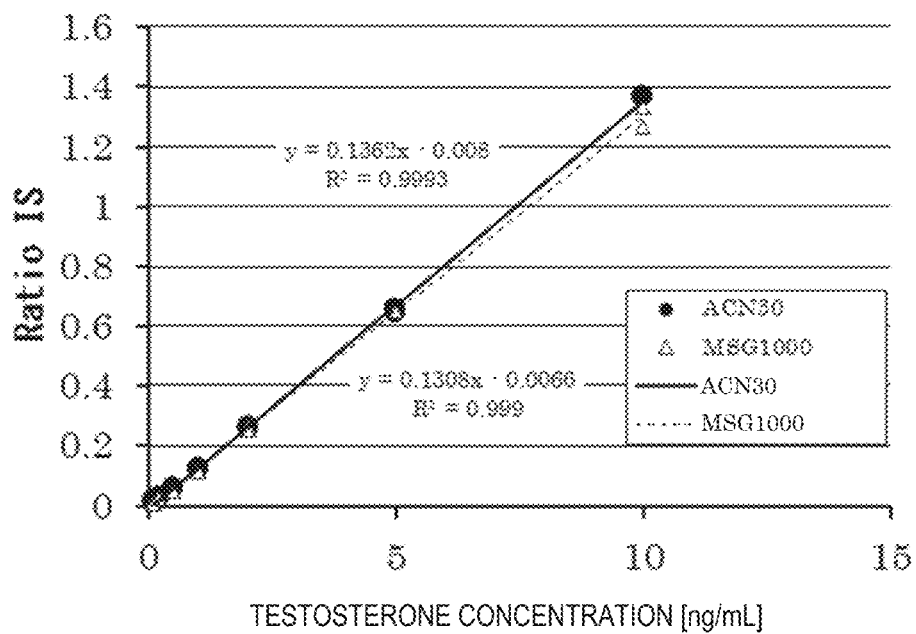
FIG. 10 is a graph of the calibration curve of testosterone in accordance with Experimental Example.

FIG. 10 illustrates a calibration curve for quantitative analysis formed using testosterone (male sex hormone). The quantitative analysis of testosterone has also proven that a good agreement is shown between the case using a standard calibration solution of a serum-based solvent and the case using a standard calibration solution of a 30% acetonitrile aqueous solution as with the vitamin D metabolite.

2.6. Verification of Concentration of Non-alcoholic Solvent

Figure 11:
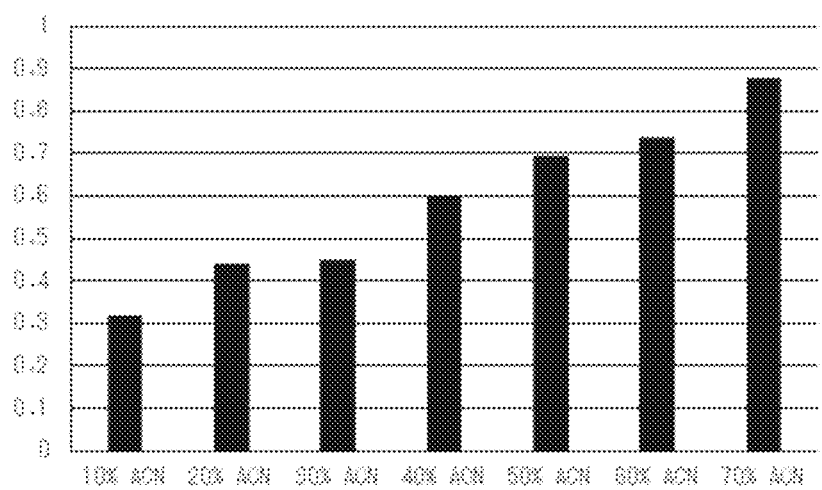
FIG. 11 is a graph illustrating the acetonitrile concentration dependency of the recovery of the internal reference material of 25(OH)$D_3$ (longitudinal axis).

FIG. 11 is a graph illustrating the dependency of the recovery of the internal reference material (IS) of 25(OH)D$_3$ on the acetonitrile concentration. It has been indicated as follows. When the acetonitrile concentration in the solvent is 10% or more, the recovery is favorable. When the acetonitrile concentration in the solvent exceeds 20%, the recovery becomes even more favorable. Further, a higher concentration of the organic solvent than that of the mobile phase in loading to a LC adversely affects the separation. From this viewpoint, it is considered that the concentration of acetonitrile in the solvent is desirably 50% or less.

2.7. Summary of Experimental Example

The results of the experiments proved the following.

The 30% acetonitrile aqueous solution-based calibrator showed a very good agreement with the serum-based calibrator. This indicated that the 30% acetonitrile aqueous solution had almost the same matrix effect as that of serum. Namely, it has been indicated that the 30% acetonitrile aqueous solution sufficiently has the performance as the calibrator medium for mass spectrometry.

The 30% acetonitrile aqueous solution includes water present therein in an amount of 70%, and hence is expected to be capable of reducing influence of the concentration due to volatilization of the solvent during storage as compared with the case using a 100% organic solvent, and is considered to be excellent in storage stability.

The invention is not limited to the above-described embodiments, and various modifications can be made. For example, the invention includes configurations that are substantially the same (for example, in function, method, and results, or in objective and effects) as the configurations described in the embodiments. The invention also includes configurations in which non-essential elements described in the embodiments are replaced by other elements. The invention also includes configurations having the same effects as those of the configurations described in the embodiments, or configurations capable of achieving the same objectives as those of the configurations described in the embodiments. The invention further includes configurations obtained by adding known art to the configurations described in the embodiments.

Some embodiments of the invention have been described in detail above, but a person skilled in the art will readily appreciate that various modifications can be made from the embodiments without materially departing from the novel teachings and effects of the invention. Accordingly, all such modifications are assumed to be included in the scope of the invention.

What is claimed is:

1. A standard calibration solution consisting of:
   water;
   a non-alcoholic solvent that is mixed with the water; and
   a steroid hormone that is endogenous to serum or plasma,
   a content of the non-alcoholic solvent being 10% by volume or more and 50% by volume or less, and
   the standard calibration solution being free of an alcoholic solvent,
   wherein the steroid hormone that is endogenous to serum or plasma is a metabolite of vitamin D.

2. The standard calibration solution according to claim 1, wherein the non-alcoholic solvent includes a compound having 5 or fewer carbon atoms and having at least one group selected from a cyano group, a carbonyl group, an ether group, and a sulfinyl group.

3. The standard calibration solution according to claim 1, wherein the non-alcoholic solvent is a compound having 3 or fewer carbon atoms and having a cyano group.

4. The standard calibration solution according to claim 1, wherein the non-alcoholic solvent is acetonitrile.

5. The standard calibration solution according to claim 1, wherein
   the metabolite of vitamin D is fat soluble, and
   a content of the non-alcoholic solvent is 20% by volume or more and 50% by volume or less.

6. The standard calibration solution according to claim 1, wherein the content of the non-alcoholic solvent is 20% by volume or more and 40% by volume or less.

* * * * *